United States Patent [19]

Jeter

[11] 4,132,776
[45] Jan. 2, 1979

[54] DELIVERY OF IMMUNOLOGICALLY ACTIVE COMPONENTS OF TRANSFER FACTOR

[75] Inventor: Wayburn S. Jeter, Tucson, Ariz.

[73] Assignee: University Patents, Inc., Norwalk, Conn.

[21] Appl. No.: 877,887

[22] Filed: Feb. 15, 1978

[51] Int. Cl.$^2$ .................... A61K 35/14; A61K 39/00; A61K 39/04
[52] U.S. Cl. ...................................... 424/101; 424/88; 424/92
[58] Field of Search ............................ 424/101, 88, 92

[56] References Cited

PUBLICATIONS

Barret–Textbook of Immunology Second Edition (1974) pp. 291–293.

*Primary Examiner*—Sam Rosen
*Attorney, Agent, or Firm*—Merriam, Marshall & Bicknell

[57] ABSTRACT

Dialyzable nucleopeptide leucocytic extracts (transfer factors), isolated from animals sensitized to selected antigenic substances, are subjected to treatment in a digestive environment and immunologically active components thereof are administered to the circulatory system of a recipient animal, preferably through digestive tract tissue, to enhance the immunological competence of the recipient.

12 Claims, No Drawings

DELIVERY OF IMMUNOLOGICALLY ACTIVE COMPONENTS OF TRANSFER FACTOR

BACKGROUND OF THE DISCLOSURE

The present invention relates generally to enhancement of the immunological competence of animals, including humans, and more specifically to improved methods for administration of immunologically active nucleopeptide substances isolated from leucocytes of a sensitized donor animal and capable of conferring or mediating immune reactions to antigenic substances. According to the invention substantial therapeutic advances may be achieved in the prevention and/or treatment of disease states in disease host animals which may be naturally immunologically incompetent.

Delayed-type hypersensitivity to tuberculin and chemicals was first transferred passively by intact peritoneal exudative leucocytes in guinea pigs in the 1940s. The inventor and his co-workers, in 1954, reported successful transfer of delayed cutaneous sensitivity to 2,4-dinitrochlorobenzene and tuberculin in guinea pigs with leucocytic extracts from cells disrupted by sonic oscillation [See, e.g., *Proc. Soc. Exp. Biol. and Med.*, 86, 251–253 (1954) and *J. Bact.*, 680–683 (1957)]. Other workers showed similar results in human beings with extracts of blood leucocytes lysed by freezing and thawing. The active component of these extracts was named "transfer factor" and many subsequent studies on the nature and functions of the transfer material have been reported. [See, e.g., *Transfer Factor: Basic Properties and Clinical Applications*, Asher, et al. (ed.), Academic Press, Inc., New York, New York (1976).]

Available evidence concerning the physical properties of transfer factors generally indicates that they are substantially non-antigenic, dialyzable materials produced in leucocytes and having a molecular weight of from about 500 to 10,000 Daltons — usually between 1500 to 5000. Transfer factors contain polypeptide and polynucleotide components and have an electrophoretic mobility similar to $\alpha$ globulins, albumins and pre-albumins. They are unaffected in activity by in vitro treatment with ribonuclease and trypsin as well as deoxyribonuclease. Similar treatment with snake venom phosphodiesterase and certain non-specific proteases (e.g., Pronase, Type VI, Sigma Chemical Co.,) has been observed to interfere with passive transfer capacity. Transfer factors are generally believed to lack sulfur-containing amino acids and solutions give a 260/280 nm optical density ratio which averages from about 0.20 to about 0.80.

Transfer factors are ordinarily isolated directly from disrupted leucocytes of a donor animal, preferably an animal sensitized to a selected antigenic chemical or biological substance including whole, or fractionated extracts of, live or killed infectious microbial materials such as bacteria, viruses, rickettsiae, fungi, protozoa and the like. Collection of leucocytes for isolation of transfer factor materials is frequently accomplished by separation of cells from whole blood, spleen or lymph node tissue or artificially-induced intraperitoneal exudates. Recent developments in processes for securing transfer factors have included isolation of transfer factor fractions from plasma of sensitized donor animals to whom a lympholytic material such as heterologous antilymphocytic serum or globulin has been administered for the purpose of disrupting the structural integrity of leucocytes in vivo.

Transfer factors transmit, upon administration to the general circulatory system of a recipient animal, specific cell-mediated immunity to antigenic substances. The precise mode of operation of transfer factors is as yet not clearly illucidated. It is not known, for example, whether the dialysate materials commonly known as transfer factors are essentially purely nucleopeptides, or whether all or merely a portion of the nucleopeptide component is immunologically active. Similarly unknown is the physiological mechanism by which these non-antigenic materials rapidly interact with the recipient animal's circulatory system constituents to develop delayed-type hypersensitivity reaction to antigens. Transfer factors are presently undergoing extensive human clinical trials with some success in the treatment of certain immuno-deficiency diseases, malignancies, and chronic infections and inflammatory diseases. Therapeutic schemes in effect or under consideration include administration of transfer factors derived from homologous or heterologous species — either alone or in combination with other chemotherapeutic agents.

Due to the inherent imprecision attending quantification of a transfer factor material of any standardized purity, dosage amounts of transfer factor are expressed in terms of "units" correlated to the quantity of dialysate obtained upon extraction from a given quantity of lymphocytes. Thus a dosage expressed as $1 \times 10^8$ lymphocyte equivalents characterizes the quantity of transfer factor obtained by isolation from $1 \times 10^8$ lymphocytes obtained from a donor animal.

Present modes of administration of transfer factors are exclusively parenteral in nature with human transfer factor usually given either subcutaneously or intradermally. Recent studies with mice have indicated that transfer factor is active when administered intraperitoneally and have suggested that a similar mode of administration be attempted in humans [See, Rifkind, et al., *Infection and Immunity:* 16, pp. 258–262 (1977)]. To date intravenous administration has been avoided owing to the known substantial risks normally accompanying introduction of proteinaceous substances into the circulatory system. Indeed, potential for anaphylactic-type reactions accompanies even subcutaneous and intradermal administration to such a degree that many investigators have been reluctant to fully explore their therapeutic potential. This is so even though transfer factors isolated by dialysis are generally free of association with higher molecular weight (~10,000) polypeptides.

In a like manner oral administration of transfer factors has been avoided due to expectation of degradation, and consequent inactivation, upon exposure to a digestive environment in the alimentary canal. Based on existing knowledge of the nucleopeptide constitution of transfer factors, it might be expected that their immune-donative capacities could withstand degradation by carbohydrases (e.g., amylase in saliva) and simple esterases. Despite the apparent absence of deactivation upon in vitro response to trypsin, however, it has been uniformly believed in the art that transfer factors, like interferon, would not retain activity upon exposure to other proteolytic hydrolytic digestive enzymes in gastrointestinal secretions (e.g., pepsin, chymotrypsin, carboxypeptidase A and B) or in cells of the intestinal mucosa (e.g., the aminopeptidases). These beliefs are substantially supported by a prevailing understanding in the art that proteins, polypeptides and nucleopeptides are not directly transported across the gastro-intestinal membrane, so that even if the transfer factors were able to withstand a digestive environment, they would not be made available to the circulatory system by absorption through gastrointestinal tissue. The exceptions to this "rule" concerning intact absorption of proteinaceous substances are quite minimal. Certain neonatal animals, including humans, transitorily display a potential capacity for absorption of intact protein and immunologically active agents from colostrum and early milk. [See, Wiseman, "Absorption from the Intestine," pp. 65-67, Academic Press, New York, New York (1964) and *Schlesinger, et al., The Lancet*: September, 1977, pp. 529-532.] Also, systemic anti-inflammatory activity has been ascribed to absorption of trypsin in the human ileum when there delivered in small, enteric-coated doses (See, U.S. Pat. No. 3,004,893).

In sum, transfer factors are presently recognized in the art as substances possessing substantial therapeutic potential but which are as yet incompletely characterized as to immunologically active components or mode of operation, and which are subject to substantial limitations in available modes of safe delivery to animals, including humans.

For purposes of providing a better understanding of background of the invention and particularly the therapeutic uses of transfer factors, the disclosures of commonly owned, co-pending U.S. Application Ser. No. 813,584, filed July 7, 1977, are expressly incorporated by reference herein.

BRIEF SUMMARY

The present invention is an improvement in the mode of delivery of immunologically active components of dialyzable nucleopeptide leucocytic extracts — transfer factors — to the circulatory system of a recipient animal. According to the invention, an extract is subjected to treatment in a digestive environment, preferably within the digestive tract of the recipient animal, and administered to the animal's circulatory system through digestive tract tissue. According to one aspect of the invention, an extract is subjected to treatment in a digestive environment by introduction into the alimentary canal of the recipient animal, whereby the digestive materials of the canal operate upon the extract. Within such a digestive environment, extraneous polypeptide and/or polynucleotide materials which are not essential to activity of the immunologically active components of the extract (but which are normally associated therewith upon isolation from leucocytes) may be degraded and yet no inactivation of the active components is observed. The active components are thereafter absorbed through digestive tract tissues and enter the circulatory system. Alternatively, the extract may be treated in vitro under conditions substantially duplicating the digestive environment of the recipient animal and thereafter administered to the animal — either orally or, after suitable isolative procedures, parenterally.

DETAILED DESCRIPTION

As employed herein, the terms "dialyzable nucleopeptide," "leucocytic extract" and "dialyzable nucleopeptide extract isolated from leucocytes" shall be employed essentially synonymously and shall mean and include substances commonly referred to in the art as "transfer factors" derived by isolation from leucocytes (or plasma-containing disrupted leucocytes) of a donor animal — preferably previously sensitized to a selected antigenic substance — and having physical and physiological characteristics substantially as described above. "Selected antigenic substance" shall mean and include natural or synthetic materials capable of evoking an immune-type response in an animal, including, but not limited to, chemical substances (e.g., 2,4-dinitrochlorobenzene) and biological substances (e.g., while or fragmentary, live or killed bacteria, viruses, rickettsiae, fungi and protozoa and/or metabolic products thereof). "Digestive environment" shall mean and include conditions substantially duplicating those commonly present within the digestive tract of an animal, including, but not limited to, pH and temperature conditions and the presence of one or more hydrolytic, phosphorylytic, oxidation-reduction, transferring, decarboxylating, hydrating or isomerizing enzymes.

As employed herein, "alimentary canal" and "digestive tract" shall be essentially synonymous and shall mean and include that anatomical portion of an animal, e.g., the mouth, pharynx, stomach, duodenum, jejunum, ileum and large intestine in humans, wherein digestive processes occur. "Parenteral administration" shall mean and include administration to an animal by means other than introduction into the alimentary canal. "Circulatory system" shall mean and include the hematic and/or lymphatic system of an animal.

The following examples serve to illustrate practice of the invention wherein a pertinent nucleopeptide dialyzable leucocyte extract, of homologous or heterologous species origin, is delivered to the circulatory system by administration to the alimentary canal of a recipient animal, wherey the extract is subjected to a digestive environment in the recipient prior to the absorption of the pertinent immunologically active component through alimentary canal wall tissues.

EXAMPLE I

Tranfer of Delayed Hypersensitivity to Tuberculin in Humans

A. Nucleopeptide Leucocyte Dialysate

An 1100-pound cow was given intradermal injections of 25 mg of heat-killed *Mycobacterium tuberculosis*, H37RV strain, in 3.0 ml sterile mineral oil at two week intervals. No more than 0.2 ml of the material was placed in any single site. Two weeks after the last sensitizing dose, the animal was skin tested by intradermal injection with Old Tuberculin, Human, Concentrated (Eli Lilly & Co.) (OT) and Purified Protein Derivative (PPD) (Parke-Davis), 0.2 mg. Skin reactions were read at 48 and 96 hours after test and judged to be strongly positive.

Two days later, the animal was bled by venipuncture from the jugular vein for approximately 4000 ml, using 10 units of heparin per ml. While blood cell counts showed 8,000 cells per cu mm of which 60% were found to be lymphocytes by differential stain. Buffy coat cells were separated by centrifugation at 1100 $\times$ g at 4° C. for 40 minutes. The separated cells were resuspended in distilled water and disrupted by freezing and thawing for 10 times using a dry ice-acetone mixture for freezing and a 37° C. water bath for thawing. Cellular debris was removed by centrifugation at 13,000 $\times$ g for 20 minutes at 4° C., and clear supernatant liquid placed in a dialysis bag (Visking casing) under vacuum for 48 hours at 4° C. Sodium chloride was added to 0.15M concentration. The dialysate was lyophilized and stored at −20° C. until used. Each dose was calculated on the basis of 1 $\times$ 10$^9$ lymphocyte equivalents.

In a similar manner a nucleopeptide leucocyte dialysate was isolated from a tuberculin negative cow and a tuberculin positive human donor (the inventor).

B. Delivery

Healthy adult human volunteers of both sexes were skin-tested with intradermal injections of 0.1 ml of PPD (Connaught), 5 TU. Test reactions were observed at 24 and 48 hours. In the first group of experiments, persons showing a negative response to this test dose were given dialysate to drink and 48 hours later retested with the same material.

The second group was retested with second strength PPD, 250 TU. Those giving no response to this test dose were given either tuberculin positive dialysate from cattle, human tuberculin positive dialysate, dialysate from tuberculin negative cattle or saline. One week later they were skin-tested again with the stronger tuberculin. All recipients were bled by venipuncture for 20 ml before ingestion of material and immediately prior to the post transfer factor skin test.

Bottles containing all three pertinent dialysates and saline were coded by number. Neither the volunteers nor the skin test observers knew what any test subject received until the test was completed. All subjects were given an explanation of the procedures, risks, etc. and participated with informed consent.

C. Results

In the first group of experiments, four persons participated who previously responded negatively to PPD, 5 TU. All drank the dialysate in 0.15 M NaCl, 30 ml and $1 \times 10^9$ lymphocyte equivalents. On skin test 48 hours later with PPD, 5 TU, three subjects showed erythema and induration greater than 10 mm in diameter, whereas the fourth was negative.

In the second group, three volunteers gave negative reactions to PPD, 5 TU. Two of these, in addition to the negative reactor in the first group, were given $2 \times 10^9$ lymphocyte equivalents (2 dose) orally in 30 ml. The third individual received $1 \times 10^9$ lymphocyte equivalents of human tuberculin positive dialysate. Skin tests with PPD, 250 TU, administered 48 hours later and read at 24 and 48 hours showed positive reactions from 12-25 mm in diameter in all subjects. Of interest was the fact that two persons showed "lighting up" at the site of the initial skin test given one week previously. One person showed an early response which graded into a typical delayed-type skin reaction. The previously negative recipient who was given a second dose converted.

The next group of experiments was set up as a double blind design. To date, 14 individuals have been tested in this group. The recipients were all negative reactors to PPD, 250 TU, at 48 hours. Eight individuals received $1.5 \times 10^9$ lymphocyte equivalents of tuberculin positive cattle dialysate and were skin-tested one week after ingestion of the material with PPD, 250 TU. Seven of the recipients showed positive skin tests ranging from $10 \times 20$ mm to $40 \times 45$ mm indurated, erythematous area on skin test one week after ingestion of the dialysate. The eighth individual converted after a second dose was given one week later.

Two of the saline controls showed no change, and the three tuberculin negative cattle dialysate recipients gave similar results. One of the saline controls gave a positive reaction of $17 \times 18$ mm.

EXAMPLE II

Transfer of Delayed Hypersensitivity to Tuberculin in Guinea Pigs

Normal guinea pigs (not previously skin tested) were given the transfer factor to tuberculin from the cow previously described. This transfer factor was administered orally to the animal, using a syringe and retainer to keep the mouth open.

One week after ingestion of this material, the animals were skin tested with 0.1 Old Tuberculin, 1:50, in 0.15 M NaCl solution. Four animals tested showed a skin test reaction of an erythematous, indurated area $10 \times 10$ mm or greater.

The foregoing examples clearly demonstrate the efficacy of practice of the invention in humans and a representative lower animal species. Practice of the invention with other species of recipient animals (e.g., dogs, rabbits, mice, bovines) and other sensitizing agents are presently contemplated and is expected to yield comparable results.

The mechanism of action of the delivery mode of the invention is not fully understood but is not believed essential to the understanding and practice thereof. According to one hypothesis, the extract is subjected to substantial degradation in the digestive environment of the recipient animal's alimentary canal, but a lower molecular weight, immunologically active component thereof is nonetheless preserved and absorbed through the gastric or intestinal mucosa. Alternatively, an entire nucleopeptide comprises the immunologically active component of the dialysate and is both substantially undegraded in the digestive environment and absorbed substantially intact through digestive tract tissue. In any event, extraneous polynucleotide and polypeptide materials associated with the nucleopeptide beyond dialysis and which are extraneous to the transfer factor's activity are rendered immunologically (and hence toxicologically) insignificant.

According to another aspect of the invention, a specific leucocyte dialysate may be efficaciously pretreated under digestive conditions and administered to the recipient animal's circulatory system. Such practice involves isolating a leucocytic extract and "pre-digesting" it in vitro in a suitable digestive environment comprising, e.g., a strongly acidic solution of pepsin and/or solutions or suspensions of the various enzymatic substances operative in digestive processes. If the digestive environment substantially duplicates that of a proposed recipient animal, the entire combination of reagents, reactants, and products may be administered to the alimentary canal of the recipient to effect delivery of the immunologically active component of the dialysate to the circulatory system. Alternatively, the resultant "digested" extract containing the active component may be separated as smaller molecular weight components from the digestive environment (e.g., by dialysis) and administered orally or parenterally. In either event, the active component will be suitably rapidly incorporated into the recipient animal's circulatory system in a manner essentially eliminating the risks of adverse reaction which ordinarily accompany the introduction of "foreign," undergraded polypeptides and polynucleotides.

Upon consideration of the foregoing description and illustrative examples, numerous modifications and variations in the practice of the invention are expected to occur to those skilled in the art. As one example, dosage amounts varying from about $1 \times 10^8$ to about $1 \times 10^{10}$ lymphocyte equivalents are suitably employed in therapeutic uses. As another example, numerous pharmaceutically acceptable carrier substances may be combined with the dialysate prior to administration and the dialysates may be administered in combination with other chemotherapeutic agents to compliment or enhance their therapeutic effectiveness. Consequently, only such limitations as appear in the appended claims should be placed thereon.

What is claimed is:

1. In the method for enhancing the immunological competance of an animal's response to a selected antigenic substance wherein transfer factor isolated from leucocytes of a donor animal sensitized to said antigenic substance is provided to the circulatory system of an animal in need of such enhancement, an improvement in delivery of an immunologically active component of said transfer factor to the circulatory system of an animal comprising: administering to the alimentary canal of a recipient animal from about $1 \times 10^8$ to about $1 \times 10^{10}$ lymphocyte equivalents of said transfer factor in a pharmaceutically acceptable carrier, whereby said transfer factor is subject to a digestive environment in the recipient animal's digestive tract and the immunologically active component of said transfer factor is absorbed through the digestive tract tissue and transported to the animal's circulatory system.

2. The improvement of claim 1 wherein the donor and recipient animals are of the same species.

3. The improvement of claim 1 wherein the quantity of transfer factor administered is about $1 \times 10^9$ lymphocyte equivalents.

4. The improvement of claim 1 wherein said pharmaceutically acceptable carrier is a saline solution.

5. The improvement of claim 1 wherein the transfer factor administered is isolated from the blood of said donor animal.

6. The improvement of claim 1 wherein the transfer factor administered is isolated from the spleen tissue of the donor animal.

7. The improvement of claim 1 wherein the transfer factor is isolated from the lymph node tissue of the donor animal.

8. The improvement of claim 1 wherein the transfer factor administered is isolated from an intraperitoneal exudate of the donor animal.

9. An improved method for delivery of an immunologically active component of a transfer factor which is isolated as a leucocytic extract of a donor animal sensitized to a selected antigenic substance, said method comprising subjecting said extract to treatment in a digestive environment to substantially free the active component therein from extraneous polypeptide or polynucleotide materials normally associated with said active component in said extract, and administering the resultant treated extract to the circulatory system of a recipient animal.

10. The method of claim 9 wherein said treatment and administration steps jointly comprise introduction of the extract into the alimentary canal of the recipient animal.

11. The method of claim 9 wherein said treatment step is carried out in vitro and the resultant treated extract is reclaimed from said digestive environment prior to said administration step.

12. The method of claim 11 wherein said administration step includes parenteral administration of said reclaimed extract.